United States Patent [19]

Nisato et al.

[11] Patent Number: 4,521,428
[45] Date of Patent: Jun. 4, 1985

[54] ANOREXIGENIC TRIFLUOROMETHYLPHENYLTETRAHYDROPYRIDINES AND PHARMACEUTICAL COMPOSITIONS CONTAINING THEM

[75] Inventors: Dino Nisato, Pavia; Marco Frigerio, Mantova; Giovanna F. Miranda, Milan, all of Italy

[73] Assignee: Sanofi, Paris, France

[21] Appl. No.: 523,565

[22] Filed: Aug. 16, 1983

[30] Foreign Application Priority Data

Aug. 16, 1982 [FR] France ................. 82 14169

[51] Int. Cl.$^3$ ............... C07D 401/06; A61K 31/44
[52] U.S. Cl. .............................. 514/277; 546/346; 546/255; 514/334; 514/335
[58] Field of Search .............. 546/255, 346; 424/263

[56] References Cited

U.S. PATENT DOCUMENTS 4,213,989 7/1980 Nedelec et al. ............... 546/346
4,472,408 9/1984 Nisato et al. ................. 546/346

FOREIGN PATENT DOCUMENTS 984364 7/1962 United Kingdom .

*Primary Examiner*—Jane T. Fan
*Attorney, Agent, or Firm*—Stevens, Davis, Miller & Mosher

[57] ABSTRACT

Novel 4-(3-trifluoromethylphenyl)-1,2,3,6-tetrahydropyridines of formula

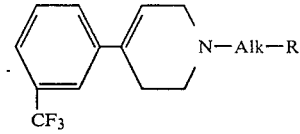

wherein R is an unsubstituted or by an alkyl group of from 1 to 4 carbon atoms substituted pyridyl, pyridyl 1-oxide or naphthyl group and Alk is a straight or branched chain alkylene group of from 2 to 4 carbon atoms are anorexigenic agents useful for treating obesity.

12 Claims, No Drawings

ANOREXIGENIC TRIFLUOROMETHYLPHENYLTETRAHYDROPYRIDINES AND PHARMACEUTICAL COMPOSITIONS CONTAINING THEM

The present invention discloses novel anorexigenic compounds.

More particularly the invention relates to novel 4-(3-trifluoromethylphenyl)-1,2,3,6-tetrahydropyridines of formula

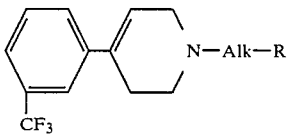

wherein R represents an unsubstituted or by an alkyl group of from 1 to 4 carbon atoms substituted pyridyl, pyridyl 1-oxide or naphthyl group and Alk represents a straight or branched chain alkylene group of from 2 to 4 carbon atoms, as well as to their pharmaceutically acceptable acid addition salts having a remarkable anorectic activity.

The products of formula I wherein R is a pyridyl 1-oxide group are particularly preferred.

It is known that the leading anorexigenic compound is amphetamine which exerts its activity by a central biochemical mechanism of action at the level of the dopaminergic and noradrenergic systems.

Amphetamine and its derivatives present important inconveniences because their stimulating effect on the central nervous system as well as the possibility of tolerance and drug-dependence may represent a potential danger for the patient.

Studies have therefore been devoted to the search for amphetamine derivatives showing a dissociation between the stimulating effect and the anorectic action. The introduction of a trifluoromethyl group in the "meta" position of the phenyl group of ethylamphetamine have led to a product, hereinafter designated by its International Nonproprietary Name "fenfluramine", having excellent anorectic activity, which, instead of being stimulant, has some sedative action.

The advantage of fenfluramine and of its derivatives over amphetamine and its derivatives is due to the different mechanism of action. In fact, the anorexia induced by amphetamine seems to be mediated by the release of cerebral noradrenaline, whilst the anorectic action of fenfluramine depends on the release of the endogenous serotonin of the central neurons (Ann. C. Sullivan et al., Appetite Regulation and its Modulation by Drugs, NUTRITION AND DRUG INTERRELATION, 1978, Academic Press, 21–82) and on the inhibition of the serotonin uptake.

However, it is known that fenfluramine, at doses very close to the anorectic dose, induces a significant reduction in the cerebral rates of serotonin (Arch. Intern. Pharmacodyn. Ther. 1967, 170, 276) and that a lasting depletion of serotonin may be considered as a sign of potential neurotoxicity (C. D. Morgan et al., Life Sci. 1972, Part I, 11, 83).

It has now been found that the 4-(3-trifluoromethylphenyl)-1,2,3,6-tetrahydropyridines of formula I hereinabove and their salts show a noteworthy anorectic activity associated with a very low toxicity. From the biochemical standpoint, the compounds of formula I hereinabove, as well as their salts, have a mechanism of action different from that of amphetamine and fenfluramine because they do not induce any stimulation of the central nervous system nor any release of neuronal serotonin. More particularly, the compounds of formula I above show a great affinity for the post-synaptic receptors of serotonin entailing an anorectic activity without the side effects due to the serotonin depletion.

Thus, it is an object of the present invention to provide novel 4-(3-trifluoromethylphenyl)-1,2,3,6-tetrahydropyridines of formula I hereinabove, as well as their pharmaceutically acceptable acid addition salts.

Pharmaceutically acceptable acid addition salts include the non-toxic salts derived from mineral or organic acids such as hydrochloride, hydrobromide, succinate, tartrate, citrate, fumarate, maleate, 4,4'-methylene-bis-(3-hydroxy-2-naphtoate), 2-naphthalenesulfonate, methanesulfonate, p-toluenesulfonate and the like.

It is another object of the present invention to provide a process for the preparation of 4-(3-trifluoromethylphenyl)-1,2,3,6-tetrahydropyridines of formula I hereinabove and of the salts thereof.

Said process comprises reacting the 4-(3-trifluoromethylphenyl)-1,2,3,6-tetrahydropyridine of formula

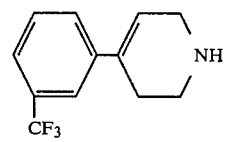

with a compound of formula X—R wherein R is as defined hereinabove and X represents a chloro-, bromo- or iodoalkyl group of from 1 to 4 carbon atoms or an electrophilic group, such as the methanesulphonyloxy or p-toluenesulphonyloxy group, or when R is other than optionally substituted naphthyl, an unsubstituted or by 1 or 2 methyl groups or by an ethyl group substituted vinyl group in an organic solvent at a temperature of from 20° to 200° C.

The 4-(3-trifluoromethylphenyl)-1,2,3,6-tetrahydropyridine used as starting material is well known in the literature.

The preferred organic solvent used is an aliphatic alcohol of from 1 to 6 carbon atoms, such as methanol, ethanol, n-butanol, n-pentanol, but other solvents such as hexane, dimethylformamide, dimethylsulfoxide, sulfolane, acetonitrile, pyridine and the like may be employed.

The reaction is advantageously carried out in the presence of a basic condensing agent such as triethylamine, especially when the reagent R—X is a halo derivative.

The reaction temperature may vary between the room temperature (about 20° C.) and 200° C. and the reaction times vary accordingly. After 4–5 hours at 100°–150° C., the reaction is generally over and the final product thus obtained may be isolated according to conventional techniques and optionally converted into its salts by simple salification in an organic solvent, such as an alcohol, preferably ethanol or isopropanol, an ether such as 1,2-dimethoxyethane, ethyl acetate or an hydrocarbon such as hexane.

According to another of its aspects, the present invention provides a process for the preparation of compounds of formula I hereinabove in which Alk is a straight chain, namely compounds of formula

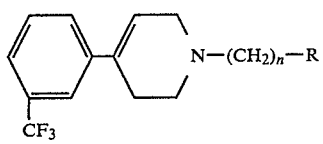

III wherein R is as defined hereinabove and n is 1,2,3 or 4, which comprises reducing a compound of formula

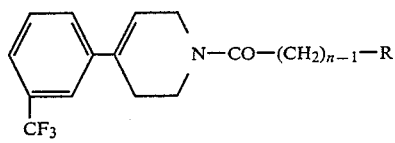

IV wherein R and n are as defined above, by an aluminium hydride or by a lithium and aluminium hydride complex in an inert organic solvent at a temperature of from 0° C. to the boiling temperature of the solvent employed and optionally converting the product thus obtained into its pharmaceutically acceptable acid addition salts.

The reduction is carried out according to known methods by using aluminium hydride or a lithium and aluminium hydride complex, such as $LiAlH_4$, $LiAlH(OCH_3)_3$ and the like as a reducing agent. The reduction is generally carried out in an inert solvent such as an ether, i.e. diethyl ether, tetrahydrofuran, dioxan or 1,2-dimethoxyethane.

According to a preferred embodiment, the reduction of the starting compound IV is carried out with an equimolecular amount of lithium and aluminium hydride $LiAlH_4$ at a temperature of 20°-30° C., in diethyl ether and in an inert atmosphere. After about one hour, the reduction is complete and the compound of formula III is isolated according to conventional techniques in the form of free base or of one ot its salts.

The free base may be converted into one of its salts by simple salification in an organic solvent such as an alcohol, preferably ethanol or isopropanol, an ether such as 1,2-dimethoxyethane, ethyl acetate or a hydrocarbon such as hexane.

The compounds of formula IV hereinabove are prepared by reacting the 4-(3-trifluoromethylphenyl)-1,2,3,6-tetrahydropyridine of formula II with a functional derivative of a carboxylic acid of formula:

$$R-(CH_2)_{n-1}-COOH$$

V wherein R and n are as defined hereinabove, in an organic solvent at a temperature of from −10° C. and the boiling temperature of the solvent employed.

The activated free acid, the anhydride, a mixed anhydride, an active ester or an acid halide, preferably the chloride, may be used as a suitable functional derivative. Among the active esters, the p-nitrophenyl ester is particularly preferred, but the methoxyphenyl, trityl, benzhydryl esters and the like are also suitable.

The reaction temperature may vary from −10° C. to the boiling temperature of the solvent employed, but the operation is generally carried out at room temperature or at 30°-50° C. It may be preferable to carry out the reaction in a cold medium when it is exothermic, for example when the chloride is used as a functional derivative of the benzoic acid of formula V.

An alcohol, such as methanol, or a halogenated solvent, such as methylene chloride, dichloroethane, chloroform and the like, is preferably used as reaction solvent, but other organic solvents compatible with the reagents employed, for example dioxane, tetrahydrofuran or a hydrocarbon such as hexane may also be used.

The reaction may be carried out in the presence of a proton acceptor, for example an alkaline carbonate or a tertiary amine, when hydrochloric acid or another acid forms during the reaction, but this proton acceptor is not essential for obtaining the final product.

The product which is obtained at the end of the reaction is generally an oil which may be isolated and characterized according to conventional techniques, but which may be used in the crude state for the reduction with the hydride.

The 4-(3-trifluoromethylphenyl)-1,2,3,6-tetrahydropyridines of the present invention and their salts show a remarkable and selective anorectic activity without giving any amphetamine-like effect. The selectivity of their anorectic action is demonstrated by the lack of pharmacological side effects, such as sedative or excitant activity or inhibition of the locomotor activity.

The anorectic activity was assessed by the food intake method in the rat. Female rats weighing 200 g are used, which were trained for 10 days to eat during a period of 4 hours and selected on the eighth day. At the end of the tenth day, the randomised animals were divided into a "control group" treated with the vehicle alone, and into several "treated groups". The treatment was effected by intraperitoneal or by oral route 30 minutes or 1 hour, respectively, before the presentation of the food and the amount of food taken in the course of the first hour was then measured.

Table I shows, for seven representative compounds of the invention:

the acute toxicity, expressed as LD50 in the rat by the oral or intraperitoneal route (A);

the anorectic activity, expressed as oral or intraperitoneal dose inhibiting by 50% the food intake (ID50, B);

the ratio between the acute toxicity and the anorectic activity which expresses the therapeutic index related to the acute toxicity (A/B).

The following compounds were used as representative compounds of the present invention:

1-[2-(2-pyridyl)ethyl]-4-(3-trifluoromethylphenyl)-1,2,3,6-tetrahydropyridine hydrochloride (compound of Example 1), 1-[2-(3-pyridyl)ethyl]-4-(3-trifluoromethylphenyl)-1,2,3,6-tetrahydropyridine hydrochloride (compound of Example 2), 1-[2-(4-pyridyl)ethyl]-4-(3-trifluoromethylphenyl)-1,2,3,6-tetrahydropyridine hydrochloride (compound of Example 3), 1-[2-(6-methyl-2-pyridyl)-4-(3-trifluoromethylphenyl)ethyl]-1,2,3,6-tetrahydropyridine hydrochloride (compound of Example 4), 4-[2-[4-(3-trifluoromethylphenyl)-1,2,3,6-tetrahydropyrid-1-yl]ethyl]pyridine 1-oxide hydrochloride (compound of Example 5), 1-[2-(1-naphthyl)ethyl]-4-(3-trifluoromethylphenyl)-1,2,3,6-tetrahydropyridine hydrochloride (compound of Example 6), 1-[2-(2-naphthyl)ethyl]-4-(3-trifluoromethylphenyl)-1,2,3,6-tetrahydropyridine hydrochloride (compound of Example 7).

TABLE I

| Compound | administration route | A LD50 mg/kg | B ID50 mg/kg | A/B |
|---|---|---|---|---|
| Example 1 | i.p. | 107.8 | 1.99 | 54.2 |
|  | os | 195.3 | 3.49 | 56.0 |
| Example 2 | os | 227.2 | 1.77 | 128.4 |
| Example 3 | os | 288.7 | 5.82 | 49.6 |
| Example 4 | os | 202.5 | 5.69 | 35.6 |
| Example 5 | os | ~300 | 1.71 | ~175.5 |
| Example 6 | os | >600 | 4.75 | >126.3 |
| Example 7 | os | >800 | 10.44 | >76.6 |
| Fenfluramine | i.p. | 102.1 | 1.58 | 64.6 |
|  | os | 230.9 | 2.51 | 92.0 |

It results from this table that the representative compounds of the present invention show a good anorectic activity with a low toxicity. Some compounds are, from the standpoint of the therapeutic index, superior to the reference compound.

From the biochemical standpoint, the 4-(3-trifluoromethylphenyl)-1,2,3,6-tetrahydropyridines of the present invention and their salts differ from fenfluramine and its derivatives in their mechanism of action. In fact, the compounds of the present invention have a very good affinity for the post-synaptic receptors of serotonin with very weak effect on the pre-synaptic mechanisms, such as the serotonin release on which, on the contrary, fenfluramine acts. The mechanism of action of the compounds of the present invention involves a remarkable anorectic activity and reduced side effects.

In particular, the compounds of the present invention in vivo, do not induce any depletion of serotonin at central level. Therefore, there is a minor possibility that a long term use of the compounds of the present invention induces some sides effects at central level.

Table II hereinbelow summarizes the percent cerebral rates of serotonin, compared to the controls, after intraperitoneal or oral administration of four representative compounds of the present invention. The determination of the cerebral rates, according to Curzon and Green (Br. J. Pharmacol. 1970, 39, 653) was made two hours after the administration. Fenfluramine was used as reference compound.

TABLE II

| Compound | administration route | dose mg/kg | cerebral rates of serotonin, % compared to controls |
|---|---|---|---|
| Example 1 | i.p. | 1.625 | 93 ± 7 |
|  |  | 3.25 | 85 ± 1 |
|  |  | 7.5 | 98 ± 10 |
| Example 2 | os | 2.0 | 113 ± 5 |
| Example 3 | os | 2.5 | 132** ± 7 |
|  |  | 5.0 | 134** ± 2 |
|  |  | 10.0 | 126* ± 5 |
| Example 4 | os | 5.69 | 119 ± 6 |
| Fenfluramine | i.p. | 7.5 | 53** ± 4 |
|  | os | 8.0 | 75** ± 5 |

*significant $P < 0.05$
**significant $P < 0.01$

It results from this table that the products of the present invention at a dose greater than the anorectic ID50 do not reduce the cerebral rates of serotonin, whereas fenfluramine leads to a significant reduction of the cerebral serotonin.

The affinity of the compounds of the present invention for the post-synaptic serotonin receptors was assessed according to the method of Peroutka et Snyder (Molec. Pharmacol. 1979, 16, 687) which consists in incubating rat cortex membranes with a fixed concentration of $^3$H-serotonin in the presence of different concentrations of the product. Table III shows the molar concentration of five representative compounds of the present invention which gives a 50% inhibition of the specific binding to the serotoninergic receptor (IC50), namely the measure of the capability of the product to interact with the binding of $^3$H-serotonin to its receptor. Fenfluramine was used as reference compound.

TABLE III

| Compound | $^3$H—serotonin binding (2 mcM) IC50 [M] |
|---|---|
| Example 1 | $1.2 \cdot 10^{-8}$ |
| Example 2 | $9.2 \cdot 10^{-9}$ |
| Example 3 | $5.4 \cdot 10^{-8}$ |
| Example 4 | $1.4 \cdot 10^{-8}$ |
| Example 6 | $1.5 \cdot 10^{-7}$ |
| Fenfluramine | $4.5 \cdot 10^{-6}$ |

It results from this table that the compounds of the present invention have a very high affinity for the post-synaptic serotoninergic receptors whilst the affinity of the reference compound is much weaker.

The compounds of formula I above are only slightly toxic and are useful as drugs.

Thus, it is a further object of the present invention to provide pharmaceutical compositions containing, as active ingredient, a 4-(3-trifluoromethylphenyl)-1,2,3,6-tetrahydropyridine of formula I hereinabove, as well as a pharmaceutically acceptable acid addition salt thereof.

In the pharmaceutical compositions of the present invention, for oral, sublingual, sub-cutaneous, intramuscular, intravenous, transdermic or rectal administration, the active ingredients of formula I hereinabove can be administered in dosage unit forms in admixture with conventional pharmaceutical carriers, to animals and human beings for the treatment of obesity.

Appropriate dosage unit forms of administration include forms for oral route such as tablets, capsules, powders, granules and oral solutions or suspensions and forms for sublingual and buccal administration, forms for subcutaneous administration, and forms for rectal administration.

In order to obtain the desired anorectic effect, the daily dose of active ingredient may vary from 0.1 to 100 mg per kg of body-weight.

Each unit dose may contain from 1 to 500 mg of active ingredient in admixture with a pharmaceutical carrier. This unit dose may be administered 1 to 4 times daily.

When a solid composition is prepared in the form of tablets, the main active ingredient is mixed with a pharmaceutical carrier such as gelatine, starch, lactose, magnesium stearate, talc, arabic gum and the like. The tablets may be coated with saccharose or other appropriate materials or they may be treated so that their activity is extended or delayed and that they continuously release a predetermined amount of active ingredient.

A preparation in capsules is obtained by mixing the active ingredient with a diluent and by pouring the mixture obtained in soft or hard capsules.

A preparation in the form of syrup or elixir may contain the active ingredient jointly with a possibly acaloric sweetening agent, methylparaben and propylparaben as antiseptics, as well as a flavoring agent and an appropriate dye.

Water-dispersible powders or granulates may contain the active ingredient mixed with dispersing agents or wetting agents, or suspending agents such as polyvinylpyrrolidone and the like, and with sweetening or flavoring agents as well.

For rectal administration, suppositories are prepared with binding agents melting at rectal temperature, for example, cocoa butter or polyethyleneglycols.

For parenteral administration, aqueous suspensions, isotonic saline solutions or sterile injectable solutions are used, which contain pharmacologically compatible dispersing and/or wetting agents, for example propyleneglycol or butyleneglycol.

The active ingredient may also be formulated in the form of microcapsules, possibly with one or more carriers or additives.

The compositions of the present invention may contain, together with the 4-(3-trifluoromethylphenyl)-1,2,3,6-tetrahydropyridines of the present invention or with one of their pharmaceutically acceptable acid addition salts, other active ingredients such as, for example, tranquilizers, antidepressants, hypolipemic or antidiabetic agents or other drugs which may be useful for the treatment of obesity.

The following examples illustrate the invention without, however, limiting its scope.

EXAMPLE 1

A mixture of 7.2 g of 4-(3-trifluoromethylphenyl)-1,2,3,6-tetrahydropyridine, 6.4 g of triethylamine, 5.63 g of 2-(2-chloroethyl)pyridine hydrochloride in 50 ml of ethanol is heated at reflux for 24 hours, then it is concentrated to dryness. The residue is taken up with 300 ml of diethyl ether and filtered, the solution is washed three times with 50 ml of water and dried on anhydrous sodium sulfate. By acidifying the solution thus obtained with a hydrogen chloride solution in isopropanol, a precipitate is obtained (7 g), which by crystallization from 150 ml of ethanol, gives 5 g of 1-[2-(2-pyridyl)ethyl]-4-(3-trifluoromethylphenyl)-1,2,3,6-tetrahydropyridine hydrochloride; m.p. 206°–208° C.

EXAMPLE 2

(a) A suspension of 11.3 g of p-nitrophenyl 3-pyridylacetate and 10 g of 4-(3-trifluoromethylphenyl)-1,2,3,6-tetrahydropyridine in 150 ml of ethanol is stirred 1 hour at room temperature, then concentrated under reduced pressure. The residue is dissolved in diethyl ether, the solution is washed with water, then with sodium hydroxide and again with water, dried on anhydrous sodium sulfate and concentrated. Thus, 1-(3-pyridylacetyl)-4-(3-trifluoromethylphenyl)-1,2,3,6-tetrahydropyridine (8 g) is obtained as an oil which is used for the subsequent reaction.

(b) To a suspension of 1.7 g of lithium and aluminium hydride in 30 ml of anhydrous diethyl ether a suspension of 8 g of 1-(3-pyridylacetyl)-4-(3-trifluoromethylphenyl)-1,2,3,6-tetrahydropyridine is added portionwise. The temperature is maintained below 25° C. The reaction mixture is stirred 1 hour at the same temperature and water is added slowly. After filtration, the organic solution is acidified with a saturated solution of hydrogen chloride in isopropanol. The precipitate (7 g) obtained is crystallized from a mixture isopropanol:ethanol 14:1 to yield 5 g of 1-[2-(3-pyridyl)ethyl]-4-(3-trifluoromethylphenyl)-1,2,3,6-tetrahydropyridine hydrochloride; m.p. 217°–219° C.

EXAMPLE 3

A mixture of 7.2 g of 4-(3-trifluoromethylphenyl)-1,2,3,6-tetrahydropyridine, 3.2 g of 4-vinylpyridine, 0.5 ml of acetic acid and 50 ml of 95% ethanol is heated at reflux for 6 hours, then it is concentrated to dryness. The residue is dissolved in 100 ml of acetone and filtered on charcoal. The solution, acidified with hydrogen chloride in isopropanol, yields 6 g of 1-[2-(4-pyridyl)ethyl]-4-(3-trifluoromethylphenyl)-1,2,3,6-tetrahydropyridine hydrochloride. Crystallization from isopropanol yields 5.5 g of pure product; m.p. 240°–245° C.

EXAMPLE 4

By operating as described in Example 1, 5.7 g of 4-(3-trifluoromethylphenyl)-1,2,3,6-tetrahydropyridine are reacted with 5.2 g of 2-(2-chloroethyl)-6-methylpyridine hydrochloride in the presence of 7.5 ml of triethylamine in 60 ml of ethanol at reflux for 18 hours to obtain 3.5 g of 1-[2-(6-methyl-2-pyridyl)ethyl]-4-(3-trifluoromethylphenyl)-1,2,3,6-tetrahydropyridine hydrochloride; m.p. 207°–210° C.

EXAMPLE 5

By operating as described in Example 3, 15.7 g of 4-(3-trifluoromethylphenyl)-1,2,3,6-tetrahydropyridine are reacted with 2.5 g of 4-vinylpyridine 1-oxide in 25 ml of n-pentyl alcohol at reflux for 24 hours to obtain 3.5 g of 4-[2-[4-(3-trifluoromethylphenyl)-1,2,3,6-tetrahydropyrid-1-yl]ethyl]pyridine 1-oxide hydrochloride; m.p. 158°–160° C.

EXAMPLE 6

(a) To a solution of 7.5 g of 4-(3-trifluoromethylphenyl)-1,2,3,6-tetrahydropyridine and 4.6 ml of triethylamine in 40 ml of methylene chloride, 6.75 g of 1-naphthylacetyl chloride in 30 ml of methylene chloride area added dropwise at 0° C. The mixture is stirred at 0° C. for 2 hours and water is added. The organic phase is separated, washed with water many times and concentrated under reduce pressure to give 11 g of crude product. Crystallization from 95% ethanol yields 8 g of 1-(1-naphthylacetyl)4-(3-trifluoromethylphenyl)-1,2,3,6-tetrahydropyridine; m.p. 137°–140° C.

(b) To a mixture of 1.2 g of lithium and aluminium hydride and 30 ml of anhydrous diethyl ether a suspension of 7.5 g of 1-(1-naphthylacetyl)-4-(3-trifluoromethylphenyl)-1,2,3,6-tetrahydropyridine in 100 ml of anhydrous diethyl ether is added dropwise at 25°–30° C. The mixture is stirred 2 hours at room temperature, the excess of lithium and aluminium hydride is destroyed with water and the aqueous phase is eliminated. The ethereal phase is washed with water, dried on anhydrous sodium sulfate and concentrated under reduced pressure. The residue is taken up with isopropanol, the solution is treated with a solution of hydrogen chloride in isopropanol and the precipitate is crystallized three times from absolute ethanol. Thus, 3.5 g of 1-[2-(1-naphthyl)ethyl]-4-(3-trifluoromethylphenyl)-1,2,3,6-tetrahydropyridine hydrochloride are obtained; m.p. 238°–240° C.

EXAMPLE 7

(a) By operating as described in Example 6(a), 7 g of 4-(3-trifluoromethylphenyl)-1,2,3,6-tetrahydropyridine are reacted with 6.15 g of 2-naphthylacetyl chloride in the presence of 4.15 g of triethylamine in methylene chloride to give 9 g of 1-(2-naphthylacetyl)-4-(3-trifluoromethylphenyl)-1,2,3,6-tetrahydropyridine; m.p. 125°–130° C.

(b) In the same manner as described in Example 6(b), the above product is reduced with 1.5 g of lithium and aluminium hydride to give 5.5 g of 1-[2-(2-naphthyl)ethyl]-4-(3-trifluoromethylphenyl)-1,2,3,6-tetrahydropyridine hydrochloride; m.p. 255°–260° C.

EXAMPLE 8

By operating as described in Example 1, 4-(3-trifluoromethylphenyl)1,2,3,6-tetrahydropyridine is reacted with 4-(2-chloroethyl)pyridine, 4-(3-chloropropyl)pyridine, 4-(4-chlorobutyl)pyridine, 2-(2-chloro-1-methylethyl)pyridine, 2-(2-chloro-2-methylethyl)pyridine, 4-(3-chloropropyl)pyridine 1-oxide and 4-(4-chlorobutyl)pyridine 1-oxide, respectively, to give 1-[2-(4-pyridyl)ethyl]-4-(3-trifluoromethylphenyl)-1,2,3,6-tetrahydropyridine hydrochloride;
1-[3-pyridyl)propyl]-4-(3-trifluoromethylphenyl)-1,2,3,6-tetrahydropyridine hydrochloride;
1-[4-(4-pyridyl)butyl]-4-(3-trifluoromethylphenyl)-1,2,3,6-tetrahydropyridine hydrochloride;
1-[2-(2-pyridyl)propyl]-4-(3-trifluoromethylphenyl)-1,2,3,6-tetrahydropyridine hydrochloride;
1-[1-methyl-2-(2-pyridyl)ethyl]-4-(3-trifluoromethylphenyl)-1,2,3,6-tetrahydropyridine hydrochloride;
4-[3-[4-(3-trifluoromethylphenyl)-1,2,3,6-tetrahydropyrid-1-yl]propyl]pyridine 1-oxide hydrochloride; and
4-[4-[4-(3-trifluoromethylphenyl)-1,2,3,6-tetrahydropyrid-1-yl]butyl]pyridine 1-oxide hydrochloride.

In the same manner, 4-(3-trifluoromethylphenyl)-1,2,3,6-tetrahydropyridine is reacted with 1-(2-chloroethyl)naphthalene, 1-(3-chloropropyl)naphthalene, 1-(4-chlorobutyl)naphthalene, 2-(2-chloroethyl)naphthalene, 2-(3-chloropropyl)naphthalene, 2-(4-chlorobutyl)naphthalene and 2-(2-chloropropyl)naphthalene, respectively, to give 1-[2-(1-naphthyl)ethyl]-4-(3-trifluoromethylphenyl)-1,2,3,6-tetrahydropyridine hydrochloride;
1-[3-(1-naphthyl)propyl]-4-(3-trifluoromethylphenyl)-1,2,3,6-tetrahydropyridine hydrochloride;
1-[4-(1-naphthyl)butyl]-4-(3-trifluoromethylphenyl)-1,2,3,6-tetrahydropyridine hydrochloride;
1-[2-(2-naphthyl)ethyl]-4-(3-trifluoromethylphenyl)-1,2,3,6-tetrahydropyridine hydrochloride;
1-[3-(2-naphthyl)propyl]-4-(3-trifluoromethylphenyl)-1,2,3,6-tetrahydropyridine hydrochloride;
1-[4-(2-naphthyl)butyl]-4-(3-trifluoromethylphenyl)-1,2,3,6-tetrahydropyridine hydrochloride and
1-[1-methyl-2-(2-naphthyl)ethyl]-4-(3-trifluoromethylphenyl)-1,2,3,6-tetrahydropyridine hydrochloride.

EXAMPLE 9

(a) According to the procedure described in Example 6(a), 4-(3-trifluoromethylphenyl)-1,2,3,6-tetrahydropyridine is reacted with 2-pyridylacetyl chloride, 3-(2-pyridyl)propionyl chloride, 1-naphthylacetyl chloride, 2-(1-naphthyl)propionyl chloride, 2-naphthylacetylchloride and 2-(2-naphthyl)propionyl chloride in methylene chloride to give 1-(2-pyridylacetyl)-4-(3-trifluoromethylphenyl)-1,2,3,6-tetrahydropyridine;
1-[3-(2-pyridyl)propionyl]-4-(3-trifluoromethylphenyl)-1,2,3,6-tetrahydropyridine;
1-(1-naphthylacetyl)-4-(3-trifluoromethylphenyl)-1,2,3,6-tetrahydropyridine;
1-[3-(1-naphthyl)propionyl]-4-(3-trifluoromethylphenyl)-1,2,3,6-tetrahydropyridine;
1-(2-naphthylacetyl)-4-(3-trifluoromethylphenyl)-1,2,3,6-tetrahydropyridine; and
1-[3-(2-naphthyl)propionyl]-4-(3-trifluoromethylphenyl)-1,2,3,6-tetrahydropyridine.

(b) According to the procedure described in Example 6(b), the products thus obtained are reduced with lithium and aluminium hydride to give 1-[2-(2-pyridyl)ethyl]-4-(3-trifluoromethylphenyl)-1,2,3,6-tetrahydropyridine hydrochloride;
1-[3-(2-pyridyl)propyl]-4-(3-trifluoromethylphenyl)-1,2,3,6-tetrahydropyridine hydrochloride;
1-[2-(1-naphthyl)ethyl]-4-(3-trifluoromethylphenyl)-1,2,3,6-tetrahydropyridine hydrochloride;
1-[3-(1-naphthyl)propyl]-4-(3-trifluoromethylphenyl)-1,2,3,6-tetrahydropyridine hydrochloride;
1-[2-(2-naphthyl)ethyl]-4-(3-trifluoromethylphenyl)-1,2,3,6-tetrahydropyridine hydrochloride and
1-[3-(2-naphthyl)propyl]-4-(3-trifluoromethylphenyl)-1,2,3,6-tetrahydropyridine hydrochloride.

EXAMPLE 10

Capsules comprising one of the products of Examples 1 to 9, having the following composition:

| active substance | 15 mg |
| --- | --- |
| lactose | 120 mg |
| magnesium stearate | 5 mg | are prepared by mixing intimately charges of the ingredients above and introducing the mixture into hard gelatine capsules.

EXAMPLE 11

Tablets comprising one of the products of the Examples 1 to 9, having the following composition:

| active substance | 20 mg |
| --- | --- |
| lactose | 100 mg |
| microcrystalline cellulose | 30 mg |
| dried corn starch | 40 mg |
| magnesium stearate | 5 mg | are prepared by crushing the active ingredient to a particle dimension of 0,4 mm size, by passing it through a 0,4 mm sieve, by mixing the crushed mixture with the other constituents and compressing to form the tablets.

In the same manner, tablets containing 40 mg of active substance are prepared.

EXAMPLE 12

By operating as described in Example 11 hereinabove, tablets having the following composition are prepared:

| active substance | 50 mg |
| --- | --- |
| lactose | 95 mg |
| cornstarch | 100 mg |
| talc | 4.5 mg |
| magnesium stearate | 0.5 mg |

EXAMPLE 13

Suppositories are prepared, having the following composition:

| active substance | 50 mg |
|---|---|
| lactose | 250 mg |
| mass for suppositories to | 1.7 g |

The active substance is mixed with the lactose and the mixture is placed uniformly in suspension in the molten mass for suppositories. The suspension is poured into cooled moulds to form suppositories weighing 1.7 g.

We claim:

1. A 4-(3-trifluoromethylphenyl)-1,2,3,6-tetrahydropyridine of formula

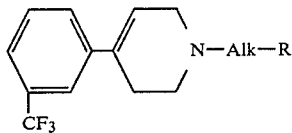

wherein R represents an unsubstituted or by an alkyl group of from 1 to 4 carbon atoms substituted pyridyl, pyridyl 1-oxide or naphthyl group and Alk represents a straight or branched chain alkylene group of from 2 to 4 carbon atoms; or a pharmaceutically acceptable acid addition salt thereof.

2. The 4-[2-[4-(3-trifluoromethylphenyl)-1,2,3,6-tetrahydropyrid-1-yl]ethyl]pyridine 1-oxide or a pharmaceutically acceptable acid addition salt thereof.

3. The 4-[2-[4-(3-trifluoromethylphenyl)-1,2,3,6-tetrahydropyrid-1-yl]ethyl]pyridine 1-oxide hydrochloride.

4. The 1-[2-(2-pyridyl)ethyl]-4-(3-trifluoromethylphenyl)-1,2,3,6-tetrahydropyridine hydrochloride.

5. The 1-[2-(3-pyridyl)ethyl]-4-(3-trifluoromethylphenyl)-1,2,3,6-tetrahydropyridine hydrochloride.

6. The 1-[2-(4-pyridyl)ethyl]-4-(3-trifluoromethylphenyl)-1,2,3,6-tetrahydropyridine hydrochloride.

7. The 1-[2-(6-methyl-2-pyridyl)ethyl]-4-(3-trifluoromethylphenyl)-1,2,3,6-tetrahydropyridine hydrochloride.

8. The 1-[2-(1-naphthyl)ethyl]-4-(3-trifluoromethylphenyl)-1,2,3,6-tetrahydropyridine hydrochloride.

9. The 1-[2-(2-naphthyl)ethyl]-4-(3-trifluoromethylphenyl)-1,2,3,6-tetrahydropyridine hydrochloride.

10. A pharmaceutical composition having anorexigenic activity containing an effective amount of a compound as claimed in any one of claims 1 to 9 in admixture with a pharmaceutical carrier.

11. A pharmaceutical composition as claimed in claim 10, which is in dosage unit form.

12. A pharmaceutical composition as claimed in claim 11 in which the amount of active ingredient is from 1 to 500 mg per dosage unit.

* * * * *